US008841481B2

(12) United States Patent
Zanthoff et al.

(10) Patent No.: US 8,841,481 B2
(45) Date of Patent: Sep. 23, 2014

(54) USE OF FOAM BODIES IN OXIDATION REACTORS FOR PREPARING UNSATURATED ALDEHYDES OR CARBOXYLIC ACIDS

(75) Inventors: Horst-Werner Zanthoff, Mulheim an der Ruhr (DE); Nicole Brausch, Recklinghausen (DE); Franz-Felix Kuppinger, Marl (DE); Jorg Sauer, Dulmen (DE); Andreas Sabbagh, Bensheim (DE); Dennis Fruhling, Gelsenkirchen (DE); Markus Weber, Bottrop (DE); Oliver Becker, Marl (DE)

(73) Assignee: Evonik Degussa GmbH, Essen (DE)

( * ) Notice: Subject to any disclaimer, the term of this patent is extended or adjusted under 35 U.S.C. 154(b) by 807 days.

(21) Appl. No.: 13/060,599

(22) PCT Filed: Jul. 29, 2009

(86) PCT No.: PCT/EP2009/059782
§ 371 (c)(1),
(2), (4) Date: Mar. 28, 2011

(87) PCT Pub. No.: WO2010/023053
PCT Pub. Date: Mar. 4, 2010

(65) Prior Publication Data
US 2011/0166304 A1 Jul. 7, 2011

(30) Foreign Application Priority Data
Aug. 29, 2008 (DE) .................. 10 2008 044 946

(51) Int. Cl.
*C07C 45/35* (2006.01)
*C07C 57/04* (2006.01)
*B01J 37/02* (2006.01)
*C07C 5/333* (2006.01)
*C07C 51/25* (2006.01)
*B01J 23/00* (2006.01)
*B01J 19/24* (2006.01)
*B01J 35/04* (2006.01)
*B01J 8/06* (2006.01)
*B01J 23/888* (2006.01)

(52) U.S. Cl.
CPC .......... *B01J 8/067* (2013.01); *B01J 2219/0004* (2013.01); *B01J 37/0219* (2013.01); *C07C 5/333* (2013.01); *B01J 2219/2481* (2013.01); *C07C 51/252* (2013.01); *B01J 2219/00006* (2013.01); *B01J 2523/00* (2013.01); *B01J 23/002* (2013.01); *B01J 37/0225* (2013.01); *C07C 45/35* (2013.01); *B01J 19/249* (2013.01); *B01J 2219/2479* (2013.01); *B01J 2208/00221* (2013.01); *B01J 2208/025* (2013.01); *B01J 35/04* (2013.01); *B01J 2219/2453* (2013.01); *B01J 23/8885* (2013.01)
USPC ............ 562/545; 562/546; 562/547; 562/598

(58) Field of Classification Search
CPC ........ C07C 45/35; C07C 51/252; C07C 57/04
USPC ................................. 562/545, 546, 547, 598
See application file for complete search history.

(56) References Cited

U.S. PATENT DOCUMENTS

| 3,087,807 | A | 4/1963 | Allen et al. |
| 3,090,094 | A | 5/1963 | Schwartzwalder et al. |
| 3,161,670 | A | 12/1964 | Adams et al. |
| 3,670,044 | A | 6/1972 | Drehman et al. |
| 3,736,355 | A | 5/1973 | Croci et al. |
| 4,220,091 | A | 9/1980 | Israels et al. |
| 4,413,147 | A | 11/1983 | Khoobiar |
| 4,532,365 | A | 7/1985 | Khoobiar |
| 4,535,188 | A | 8/1985 | Khoobiar |
| RE32,082 | E | 2/1986 | Khoobiar |
| 4,788,371 | A | 11/1988 | Imai et al. |
| 5,151,246 | A | 9/1992 | Baumeister et al. |
| 5,430,220 | A | 7/1995 | Khare et al. |
| 5,705,684 | A | 1/1998 | Hefner et al. |
| 5,817,596 | A | 10/1998 | Akporiaye et al. |

(Continued)

FOREIGN PATENT DOCUMENTS

| DE | 1962431 A1 | 6/1970 |
| DE | 3313573 | 10/1983 |

(Continued)

OTHER PUBLICATIONS

Bub et al., U.S. Appl. No. 13/029,208, filed Feb. 17, 2011.

(Continued)

*Primary Examiner* — Yevegeny Valenrod
(74) *Attorney, Agent, or Firm* — Smith Moore Leatherwood LLP; Philip P. McCann; John P. Zimmer (57) ABSTRACT

The present invention relates to a process for preparing unsaturated aldehydes or unsaturated carboxylic acids by heterogeneous catalytic gas phase oxidation of unsaturated or saturated hydrocarbons, comprising the process steps of: i) providing a gas mixture comprising a saturated hydrocarbon and catalytically dehydrogenating the saturated hydrocarbon in the gas phase to obtain a gas mixture comprising an unsaturated hydrocarbon in a dehydrogenation reactor having a dehydrogenation catalyst material; or ii) providing a gas mixture comprising oxygen and an unsaturated hydrocarbon; iii) catalytically oxidizing the unsaturated hydrocarbon obtained in process step i) or provided in process step ii) in the gas phase to obtain a gas mixture comprising an unsaturated aldehyde in a first oxidation reactor having a first oxidation catalyst material; wherein at least one of the reactors selected from the dehydrogenation reactor, the first oxidation reactor and the second oxidation reactor comprises at least one foam body.

22 Claims, 6 Drawing Sheets

(56) References Cited

U.S. PATENT DOCUMENTS

| | | |
|---|---|---|
| 5,877,369 A | 3/1999 | Wu et al. |
| 5,922,925 A | 7/1999 | Akporiaye et al. |
| 6,232,512 B1 | 5/2001 | Haas et al. |
| 6,313,063 B1 | 11/2001 | Rytter et al. |
| 6,325,265 B1 | 12/2001 | Muench et al. |
| 6,414,209 B1 | 7/2002 | Herskowitz et al. |
| 6,441,255 B1 | 8/2002 | Haas et al. |
| 6,447,744 B1 | 9/2002 | Haas et al. |
| 6,448,439 B1 | 9/2002 | Eck et al. |
| 6,540,975 B2 | 4/2003 | Tonkovich et al. |
| 6,566,573 B1 | 5/2003 | Bharadwaj et al. |
| 6,582,589 B2 | 6/2003 | Rytter et al. |
| 6,596,881 B2 | 7/2003 | Haas et al. |
| 6,600,055 B2 | 7/2003 | Haas et al. |
| 6,616,909 B1 | 9/2003 | Tonkovich et al. |
| 6,617,465 B2 | 9/2003 | Thiele et al. |
| 6,639,108 B2 | 10/2003 | Schiffer et al. |
| 6,670,303 B1 | 12/2003 | Heineke et al. |
| 6,700,029 B2 | 3/2004 | Bogan et al. |
| 6,781,017 B2 | 8/2004 | Machhammer et al. |
| 6,794,331 B2 | 9/2004 | Ostgard et al. |
| 6,858,754 B2 | 2/2005 | Borgmeier |
| 6,867,328 B2 | 3/2005 | Borgmeier et al. |
| 6,887,809 B1 | 5/2005 | Adler et al. |
| 6,911,556 B2 | 6/2005 | Bogan et al. |
| 6,911,563 B2 | 6/2005 | Mizukami et al. |
| 6,933,407 B2 | 8/2005 | Berndt et al. |
| 7,002,050 B2 | 2/2006 | Santiago Fernandez et al. |
| 7,005,403 B2 | 2/2006 | Borgmeier et al. |
| 7,026,506 B2 | 4/2006 | Borgmeier et al. |
| 7,038,080 B2 | 5/2006 | Dieterle et al. |
| 7,038,082 B2 | 5/2006 | Dieterle et al. |
| 7,045,114 B2 | 5/2006 | Tonkovich et al. |
| 7,091,377 B2 | 8/2006 | Borgmeier et al. |
| 7,176,335 B2 | 2/2007 | Berndt et al. |
| 7,214,822 B2 | 5/2007 | Borgmeier et al. |
| 7,238,827 B2 | 7/2007 | Hechler et al. |
| 7,271,279 B2 | 9/2007 | Borgmeier et al. |
| 7,291,761 B2 | 11/2007 | Machhammer et al. |
| 7,294,734 B2 | 11/2007 | Brophy et al. |
| 7,294,741 B2 | 11/2007 | Bub et al. |
| 7,321,058 B2 | 1/2008 | Machhammer et al. |
| 7,326,802 B2 | 2/2008 | Hechler et al. |
| 7,348,443 B2 | 3/2008 | Proll et al. |
| 7,388,106 B2 | 6/2008 | Klanner et al. |
| 7,388,109 B2 | 6/2008 | Machhammer et al. |
| 7,396,956 B2 | 7/2008 | Dieterle et al. |
| 7,557,245 B2 | 7/2009 | Nordhoff et al. |
| 7,569,196 B2 | 8/2009 | Zanthoff et al. |
| 7,592,483 B2 | 9/2009 | Dieterle et al. |
| 7,632,967 B2 | 12/2009 | Ostgard et al. |
| 7,723,549 B2 | 5/2010 | Diefenbacher et al. |
| 7,803,969 B2 | 9/2010 | Nordhoff et al. |
| 2004/0220434 A1 | 11/2004 | Brophy et al. |
| 2005/0131255 A1* | 6/2005 | Benderly et al. ............ 562/546 |
| 2005/0171380 A1* | 8/2005 | Bub et al. .................... 562/545 |
| 2005/0176985 A1 | 8/2005 | Bogan et al. |
| 2005/0239643 A1 | 10/2005 | Benderly et al. |
| 2006/0001711 A1 | 1/2006 | Buchanan et al. |
| 2006/0004229 A1 | 1/2006 | Dieterle et al. |
| 2006/0029541 A1 | 2/2006 | Tonkovich et al. |
| 2006/0205586 A1* | 9/2006 | Sachweh et al. ............ 502/22 |
| 2007/0060702 A1* | 3/2007 | Gao et al. .................... 524/700 |
| 2008/0031788 A1 | 2/2008 | Brophy et al. |
| 2008/0058570 A1 | 3/2008 | Winterberg et al. |
| 2008/0058575 A1 | 3/2008 | Winterberg et al. |
| 2008/0251456 A1 | 10/2008 | Wiese et al. |
| 2008/0287616 A1 | 11/2008 | Balduf et al. |
| 2009/0023006 A1 | 1/2009 | Bub et al. |
| 2009/0134357 A1 | 5/2009 | Bub et al. |
| 2009/0239995 A1 | 9/2009 | Bub et al. |
| 2011/0028664 A1 | 2/2011 | Nordhoff et al. |
| 2011/0046297 A1 | 2/2011 | Hengstermann et al. |

FOREIGN PATENT DOCUMENTS

| | | |
|---|---|---|
| DE | 4018360 C1 | 5/1991 |
| DE | 19937105 A1 | 2/2001 |
| DE | 19937107 A1 | 2/2001 |
| DE | 19937196 A1 | 3/2001 |
| DE | 10131297 A1 | 1/2003 |
| DE | 10211275 A1 | 9/2003 |
| DE | 10245585 A1 | 4/2004 |
| DE | 102004032129 A1 | 3/2005 |
| DE | 102005009885 A1 | 9/2006 |
| DE | 102005009891 A1 | 9/2006 |
| DE | 102005010111 A1 | 9/2006 |
| DE | 102005013039 A1 | 9/2006 |
| DE | 102005022798 A1 | 11/2006 |
| DE | 102005049699 A1 | 4/2007 |
| DE | 102005052923 A1 | 5/2007 |
| EP | 0117146 | 8/1984 |
| EP | 0705136 A1 | 4/1996 |
| EP | 0731077 A2 | 9/1996 |
| EP | 1015410 A1 | 7/2000 |
| EP | 1916230 A1 | 4/2008 |
| EP | 1935868 A1 | 6/2008 |
| JP | 2002205968 | 7/2002 |
| JP | 2003201260 | 7/2003 |
| JP | 2003520674 | 7/2003 |
| JP | 2005511776 | 4/2005 |
| JP | 2005144432 | 6/2005 |
| JP | 2005305438 | 11/2005 |
| JP | 2006525334 | 11/2006 |
| WO | 9429021 A1 | 12/1994 |
| WO | 9914181 A1 | 3/1999 |
| WO | 9929420 A1 | 6/1999 |
| WO | 9946039 A1 | 9/1999 |
| WO | 0154807 A1 | 8/2001 |
| WO | 0196270 A2 | 12/2001 |
| WO | 0196271 A2 | 12/2001 |
| WO | 0220426 A1 | 3/2002 |
| WO | 0255469 A1 | 7/2002 |
| WO | 03011804 A1 | 2/2003 |
| WO | 03051809 A1 | 6/2003 |
| WO | 03076370 A1 | 9/2003 |
| WO | 03078378 A1 | 9/2003 |
| WO | 2004099113 A1 | 11/2004 |
| WO | 2006002708 A1 | 1/2006 |

OTHER PUBLICATIONS

German language International Preliminary Report on Patentability mailed on Nov. 10, 2010 in PCT/EP2009/059782.

International Search Report mailed on Feb. 17, 2010 in PCT/EP2009/059782.

Kuppinger et al., U.S. Appl. No. 12/438,295, filed Nov. 12, 2009.

English translation of Office Action dated Sep. 6, 2013 for Japanese Patent Application No. 2011-524287 (5 pages).

Japanese language article, The Society of Chemical Engineers, Japan, "Kogyo Shokubai—Gijutsu Kakushin o Umu Shokubai," copyright 2002, Baifukan Co., Ltd., pp. 8-12 (5 pages).

Japanese translation of Office Action dated Sep. 6, 2013 for Japanese Patent Application No. 2011-524287 (4 pages).

* cited by examiner

USE OF FOAM BODIES IN OXIDATION REACTORS FOR PREPARING UNSATURATED ALDEHYDES OR CARBOXYLIC ACIDS

This application is a national stage application under 35 U.S.C. 371 of International Application No. PCT/EP2009/059782 filed 29 Jul. 2009, which claims priority to German Application No. DE 10 2008 044 946.6 filed 29 Aug. 2008, the disclosures of which are expressly incorporated herein by reference.

The present invention relates to a process for preparing unsaturated aldehydes or unsaturated carboxylic acids by heterogeneous catalytic gas phase oxidation of saturated or unsaturated hydrocarbons, to a process for preparing a polymer based on an unsaturated carboxylic acid, to an apparatus for preparing unsaturated carboxylic acids or a polymer based on unsaturated carboxylic acids, and to the use of an apparatus.

Acrylic acid, as a partial oxidation product of propene, is an important monomer which finds use as such for preparing superabsorbent polymers or in the form of its alkyl esters for producing adhesives, for example (cf., for example, WO-A-02/055469 and WO-A-03/078378). Acrolein is an important intermediate, for example for the preparation of glutaraldehyde, methionine, folic acid and acrylic acid.

BACKGROUND

Methacrylic acid and methacrylic esters such as methyl methacrylate and butyl methacrylate are likewise used in a wide variety of applications. Typical end applications involve acrylic polymer webs or films, molding resins, polyvinyl chloride modifiers, processing aids, acrylic coating materials, floor care compositions, sealants, automotive transmission fluids, crank case oil modifiers, motor vehicle coatings, ion exchange resins, cement or adhesive modifiers, water treatment polymers, electronic adhesives, metal coatings and acrylic fibers.

The known industrial scale processes for preparing (meth) acrolein and/or (meth)acrylic acid (for example according to DE-A-19 62 431) by gas phase oxidation of propene or isobutene are generally performed in tube bundle reactors which have a large number (in some cases more than 30 000) reaction tubes welded in between tube plates. Preference is given here to working at temperatures between 200 and 450° C. and optionally elevated pressure. The reaction tubes are filled with the heterogeneous oxidation catalyst in the form of a fixed bed and the reaction mixture flows through them. The fixed beds preferably comprise catalyst materials which are based on mixed metal oxides and have been shaped to spheres, rings or cylinders, or else coated catalysts which have been obtained by the coating of preshaped inert support bodies with a catalytically active material.

The objective of any two-stage fixed bed gas phase oxidation of propene to acrylic acid or of isobutene to methacrylic acid, or else of a conversion of propane or isobutane to acrylic acid or methacrylic acid via a dehydrogenation followed by a two-stage fixed bed gas phase oxidation or else via a direct oxidation of the propane or isobutane, is in principle to achieve a maximum space-time yield of acrylic acid or methacrylic acid ($STY_{AA}$ or $STY_{MAA}$) (this is the total amount of acrylic acid or of methacrylic acid obtained per hour and total volume of the catalyst bed used in liters in a continuous procedure). There is therefore a general interest in performing such a two-stage fixed bed gas phase oxidation of propene to acrylic acid or of isobutene to methacrylic acid firstly with a maximum space velocity of propene or isobutene on the first fixed catalyst bed (this is understood to mean the amount of propene or isobutene in standard liters (=l (STP); the volume in liters that the corresponding amount of propene or isobutene would occupy at 25° C. and 1 bar) which is conducted as a constituent of the starting reaction gas mixture per hour through one liter of catalyst bed), and secondly with a maximum space velocity of acrolein or methacrolein on the second fixed catalyst bed (this is understood to mean the amount of acrolein or methacrolein in standard liters (=l (STP), the volume in liters that the corresponding amount of acrolein or methacrolein would occupy at 25° C. and 1 bar) which is conducted as a constituent of the starting reaction gas mixture per hour through one liter of catalyst bed), without significantly impairing the conversion of propene or isobutene and acrolein or methacrolein which proceeds in the course of single pass of the starting reaction gas mixture through two fixed catalyst beds, and the selectivity of the associated acrylic acid or methacrylic acid formation (based on propene or isobutene converted) assessed over both reaction stages.

The achievement of the above is impaired by the fact that both the fixed bed gas phase oxidation of propene or isobutene to acrolein or methacrolein and the fixed bed gas phase oxidation of acrolein or methacrolein to acrylic acid or methacrylic acid first proceeds strongly exothermically and is secondly accompanied by a variety of possible parallel and subsequent reactions. With increasing propene or isobutene velocity and with increasing acrolein or methacrolein velocity on the particular fixed catalyst bed, it therefore has to be assumed, when the desired boundary condition of an essentially uniform propene or isobutene conversion and of an essentially uniform acrolein or methacrolein conversion is achieved, that, owing to the increased production of heat, the selectivity of product of value formation decreases (see, for example, also EP-A-450 596).

In order to improve the selectivity of product of value formation, it is therefore necessary to effectively remove the heat of reaction released in the conversion of the propene or of the isobutene and that released in the conversion of the acrolein or methacrolein. In the tube bundle reactors described at the outset, at least one heat exchange medium is therefore conducted around the reaction tubes on the shell side of the tube bundle reactor, which is, for example, a salt melt.

However, the above-described prior art tube bundle reactors have numerous disadvantages.

Firstly, in spite of the use of heat exchange media, the heat of reaction released can only be removed to a limited degree in the fixed catalyst beds, which is attributable especially to the poor heat removal of the fixed beds themselves. This poor heat removal of the fixed beds currently limits the tube diameter to approx. 2.5 to 3 cm, which necessitates the use of in some cases more than 30 000 reaction tubes in order to ensure a satisfactory space-time yield. However, owing to the large number of welded joints, this high number of reaction tubes causes high capital costs. This high number of reaction tubes also causes very complex catalyst filling procedures, in which it has to be ensured that the same amount of catalyst and a comparable bulk density is introduced in each of the reaction tubes. This is important since the pressure drop is otherwise not the same in all reaction tubes. A homogeneous pressure drop in the reaction tubes is one factor which is crucial for them ensuring a homogeneous reactant conversion and the minimization of by-product formation.

Moreover, in spite of the use of the heat removal medium, even in the case of tube diameters of only 2.5 to 3 cm, a temperature profile of in some cases more than 90° C. still develops in axial direction of the reactor. This results in so-called "hotspots" (these are regions with particularly high evolution of heat) in the reaction tubes, which more particularly also limits the lifetime of the catalysts in these regions. The difference between the temperature of the heat exchange medium and of the catalyst in the hotspot increases with increasing throughput. The formation of these hotspot temperatures can also lead to a decrease in the selectivity in the product conversion. To improve the selectivity with which the target products are formed, the prior art therefore proposes performing the heterogeneously catalyzed partial gas phase oxidation of acrolein to acrylic acid or of methacrolein to methacrylic acid, the dehydrogenation of propane or isobutane to propene or isobutene, the oxidation of propene or isobutene to acrolein or methacrolein, or else the direct oxidation of propane or isobutane to acrylic acid or methacrylic acid, as a multizone method (e.g. two-zone method) in a multizone tube bundle reactor (e.g. in a two-zone tube bundle reactor). In this case, a plurality of (e.g. two) essentially spatially separate liquid heat exchange media (which are normally of the same type) are conducted within the space surrounding the reaction tubes (these may, for example, be separated by separating tube plates which are inserted within the space surrounding the reaction tubes and have corresponding passage orifices for the reaction tubes).

A further disadvantage of conventional tube bundle reactors is that variations in the temperature of the heat exchange medium have a very strong and direct effect on the temperature in the reaction region of the reaction tubes, which can easily lead to runaway of the reactors. Conventional tube bundle reactors also have the disadvantage that the main reaction takes place in the above-described hotspot regions, whereas the temperature for a reaction is usually too low in the rear part of the reactor (this makes up about ⅔ of the total length of the reactor). Therefore, a large amount of catalyst material and a long residence time are needed in the rear part of the reactor to achieve a sufficient conversion.

Finally, the fixed catalyst beds used in the tube bundle reactors known from the prior art frequently lead to a high pressure drop, which necessitates an adjustment of the compressor output.

It was an object of the present invention to overcome the disadvantages arising from the prior art in connection with the direct oxidation of saturated hydrocarbons, and disadvantages which arise with the catalytic dehydrogenation and subsequent catalytic gas phase oxidation of saturated hydrocarbons, and the catalytic gas phase oxidation of unsaturated hydrocarbons or unsaturated aldehydes.

SUMMARY

The present invention includes various embodiments as set forth herein.

More particularly, it was an object of the present invention to specify a process for preparing unsaturated aldehydes or unsaturated carboxylic acids by heterogeneous catalytic gas phase oxidation of saturated or unsaturated hydrocarbons, in which tube bundle reactors with a significantly greater diameter compared to the reaction tubes described in the prior art can be used, but it is nevertheless possible to achieve a space-time yield of (meth)acrylic acid which is comparable to the space-time yield of the tube bundle reactors known from the prior art. The process should also be operable significantly more reliably compared to the processes known from the prior art. More particularly, the formation of hotspots or the risk of runaway of the reactor should be significantly lower than in the processes known from the prior art.

It was also an object of the present invention to specify a process for preparing unsaturated aldehydes or unsaturated carboxylic acids by heterogeneous catalytic gas phase oxidation of saturated or unsaturated hydrocarbons, which can be operated with a higher throughput compared to the processes known from the prior art.

It was a further object of the present invention to specify a process for preparing unsaturated aldehydes or unsaturated carboxylic acids by heterogeneous catalytic gas phase oxidation of saturated or unsaturated hydrocarbons, in which a multizone method can optionally be dispensed with without losses with regard to selectivity and/or to conversion.

Furthermore, it was an object of the present invention to specify a process for preparing unsaturated aldehydes or unsaturated carboxylic acids by heterogeneous catalytic gas phase oxidation of saturated or unsaturated hydrocarbons, in which a higher throughput can be achieved at the same compressor output as in the processes known from the prior art. Moreover, this process should also enable the use of oxygen-enriched air or of pure oxygen in the oxidation steps.

It was also an object of the present invention to specify an apparatus for preparing unsaturated carboxylic acids, by means of which the above-described process advantages can be achieved and which can be provided with low capital costs compared to the apparatus known from the prior art. Moreover, it should be possible to fill this apparatus with the catalyst significantly more easily.

FIGURES

The foregoing and other features, aspects, and advantages of the present invention will become better understood with regard to the following description, appended claims, and accompanying drawing where:

DETAILED DESCRIPTION

A contribution to solving the problems cited at the outset is made by a process for preparing unsaturated aldehydes or unsaturated carboxylic acids by heterogeneous catalytic gas phase oxidation of unsaturated or saturated hydrocarbons, comprising the process steps of:

i) providing a gas mixture at least comprising a saturated hydrocarbon and catalytically dehydrogenating the at least one saturated hydrocarbon in the gas phase to obtain a gas mixture comprising an unsaturated hydrocarbon in a dehydrogenation reactor having a dehydrogenation catalyst material; or ii) providing a gas mixture at least comprising oxygen and at least one unsaturated hydrocarbon;

iii) catalytically oxidizing the unsaturated hydrocarbon obtained in process step i) or provided in process step ii) in the gas phase to obtain a gas mixture comprising an unsaturated aldehyde in a first oxidation reactor having a first oxidation catalyst material;

iv) optionally catalytically oxidizing the unsaturated aldehyde obtained in process step iii) in the gas phase to obtain a gas mixture comprising an unsaturated carboxylic acid in a second oxidation reactor having a second oxidation catalyst material;

wherein at least one of the reactors selected from the dehydrogenation reactor, the first oxidation reactor and the second oxidation reactor comprises at least one foam body, preferably having open cells. The foam body may either consist primarily of ceramic or metallic material or else of a mixture of ceramic and metallic material, preference being given to either ceramic or metallic material. The same also applies to the process according to the invention.

In addition to open-cell foams, closed-cell foams are known to those skilled in the art. In the case of open-cell foam, the walls between the majority, often more than 80% or essentially all, of the individual cells in the foam body are completely closed. In open-cell foam, the cell walls of most cells, often more than 50% or essentially all, in the foam body are not closed. These foams can therefore absorb or conduct liquids or gases better than closed-cell foams because most, often more than 50%, of the cells in the foam body are joined to one another.

Completely surprisingly, but no less advantageously for that, it has been found that the use of preferably open-cell, preferably metallic or ceramic foam bodies in the dehydrogenation and/or oxidation reactors allows greater throughputs to be achieved with the same reactor dimensions, and that the lifetime of the catalysts used can additionally be increased significantly. The low hotspot temperatures which result through the use of preferably open-cell foam bodies in the dehydrogenation and/or oxidation reactors additionally enable greater tube diameters and therefore low capital costs. Moreover, the use of preferably open-cell foam bodies in the oxidation reactors allows the use of catalyst beds of different activity in axial direction, the use of different cooling circuits or the use of different catalyst materials in order to ensure stable operation in the reactor to be dispensed with. Moreover, the use of preferably open-cell foam bodies in the dehydrogenation and/or oxidation reactors is associated with a lower pressure drop compared to conventional fixed beds, such that higher throughputs can be achieved at the same compressor output compared to conventional tube bundle reactors.

In a particular configuration of the process according to the invention, the saturated hydrocarbon can also be converted in a direction oxidation to the unsaturated carboxylic acid (such that process steps i), iii) and iv) proceed simultaneously in one and the same reactor). The term "direct oxidation" is intended to express that, as the reaction gas mixture comprising the saturated hydrocarbon passes through the catalyst bed, the unsaturated carboxylic acid is formed directly in each case. Accordingly, the properties of the catalyst bed are not such that, as the reaction gas mixture comprising the saturated hydrocarbon flows through the catalyst bed, principally isolable intermediates, for example unsaturated hydrocarbons or unsaturated aldehydes, are initially formed in the first longitudinal sections thereof in flow direction, from which the unsaturated carboxylic acid would not form until the further longitudinal sections of the catalyst bed which follow in flow direction. Instead, at least individual catalyst materials used in the catalyst bed are capable of catalyzing all of the different reaction steps to be passed through on the reaction path from the saturated hydrocarbon to the unsaturated carboxylic acid, such that, for example, acrylic acid can be or is formed directly from propane or methacrylic acid can be or is formed directly from isobutane over the particular catalyst materials capable thereof. In this case, only a single oxidation reactor is therefore used, and the dehydrogenation catalyst material, the first oxidation catalyst material and the second oxidation catalyst material are either identical or are at least present together, optionally as a mixture, in this one reactor, or a catalyst material capable of catalyzing all of the aforementioned reaction steps or converting them to the target product (unsaturated carboxylic acid) via another reaction route is used.

In a first particular embodiment of the process according to the invention, the process comprises process steps ii), iii) and iv). In this embodiment, the unsaturated hydrocarbon is propene, the unsaturated aldehyde acrolein and the unsaturated carboxylic acid acrylic acid. In connection with this embodiment, it is especially preferred that the dehydrogenation reactor, the first oxidation reactor, the second oxidation reactor, the dehydrogenation reactor and the first oxidation reactor, the dehydrogenation reactor and the second oxidation reactor, the first oxidation reactor and the second oxidation reactor, or the dehydrogenation reactor, the first oxidation reactor and the second oxidation reactor comprises at least one preferably open-cell, preferably metallic or ceramic, foam body.

In a second particular embodiment of the process according to the invention, the process likewise comprises process steps ii), iii) and iv). In this embodiment, the unsaturated hydrocarbon is isobutene, the unsaturated aldehyde methacrolein and the unsaturated carboxylic acid methacrylic acid. In connection with this embodiment, it is especially preferred that the dehydrogenation reactor, the first oxidation reactor, the second oxidation reactor, the dehydrogenation reactor and the first oxidation reactor, the dehydrogenation reactor and the second oxidation reactor, the first oxidation reactor and the second oxidation reactor, or the dehydrogenation reactor, the first oxidation reactor and the second oxidation reactor comprises at least one preferably open-cell, preferably metallic or ceramic, foam body.

In a third particular embodiment of the process according to the invention, the process comprises process steps i), ii), iii) and iv). In this embodiment, the saturated hydrocarbon is propane, the unsaturated hydrocarbon propene, the unsaturated aldehyde acrolein and the unsaturated carboxylic acid acrylic acid. In connection with this embodiment, it is especially preferred that the dehydrogenation reactor, the first oxidation reactor, the second oxidation reactor, the dehydrogenation reactor and the first oxidation reactor, the dehydrogenation reactor and the second oxidation reactor, the first oxidation reactor and the second oxidation reactor, or the dehydrogenation reactor, the first oxidation reactor and the second oxidation reactor comprises at least one preferably open-cell, preferably metallic or ceramic, foam body. It should be noted that, in a particular configuration of this third particular embodiment of the process according to the invention, the propane or the isobutane can also be converted by a direct oxidation to acrylic acid or to methacrylic acid.

In a fourth particular embodiment of the process according to the invention, the process comprises process steps i), ii), iii) and iv). In this embodiment, the saturated hydrocarbon is isobutane, the unsaturated hydrocarbon isobutene, the unsaturated aldehyde methacrolein and the unsaturated carboxylic acid methacrylic acid. In connection with this embodiment, it is especially preferred that the dehydrogenation reactor, the first oxidation reactor, the second oxidation reactor, the dehydrogenation reactor and the first oxidation reactor, the dehydrogenation reactor and the second oxidation reactor, the first oxidation reactor and the second oxidation reactor, or the dehydrogenation reactor, the first oxidation reactor and the second oxidation reactor comprises at least one preferably open-cell, preferably metallic or ceramic, foam body. Here too, it should be noted that, in a particular configuration of this fourth particular embodiment of the process according to the invention, the isobutene can also be converted by a direct oxidation to methacrylic acid.

In process step i) of the process according to the invention, a gas mixture at least comprising a saturated hydrocarbon is optionally first provided, and the hydrocarbon present in this gas mixture is dehydrogenated and therefore oxidized by catalytic gas phase oxidation to obtain a gas mixture comprising an unsaturated hydrocarbon in a dehydrogenation reactor having a dehydrogenation catalyst material. This saturated hydrocarbon is preferably propane or isobutane (see the above-described third and fourth particular embodiments of the process according to the invention).

Processes for preparing acrolein or acrylic acid from propane, in which propane is partially dehydrogenated under heterogeneous catalysis to propene in a first reaction zone, and then the propene formed is oxidized to acrolein, or to acrylic acid, or to a mixture thereof, are known from patents including DE-A-33 13 573, EP-A-0 117146, U.S. Pat. No. 3,161,670, DE-A-10 2004 032 129, EP-A-0 731 077, DE-A-10 2005 049 699, DE-A-10 2005 052 923, WO-A-01/96271, WO-A-03/011804, WO-A-03/076370, WO-A-01/96270, DE-A-10 2005 009 891, DE-A-10 2005 013 039, DE-A-10 2005 022 798, DE-A-10 2005 009 885, DE-A-10 2005 010 111 and DE-A-102 455 85. Likewise known are processes in which isobutane is heterogeneously partially dehydrogenated to isobutene in a first reaction zone, and then the isobutene formed is oxidized to methacrolein, or to methacrylic acid, or to a mixture thereof (see, for example, DE-A-33 13 573).

In principle, the dehydrogenation of the saturated hydrocarbon can be performed in the presence of oxygen as an exothermic oxydehydrogenation (the hydrogen pulled from the dehydrogenation reacts directly with oxygen to form water), or else as an endothermic dehydrogenation in the absence of oxygen (the dehydrogenation forms molecular hydrogen).

Useful dehydrogenation catalyst materials include in principle all dehydrogenation catalyst materials known in the prior art. They can be divided roughly into two groups: those which are of oxidic nature (for example chromium oxide and/or aluminum oxide) and those which consist of at least one generally comparatively noble metal (for example platinum) deposited on a generally oxidic support. Among others, this makes it possible to use all dehydrogenation catalyst materials described in WO-A-01/96270, EP-A-0 731 077, DE-A-102 11 275, DE-A 101 31 297, WO-A-99/46039, U.S. Pat. No. 4,788,371, EP-A-0 705 136, WO-A-99/29420, U.S. Pat. No. 4,220,091, U.S. Pat. No. 5,430,220, U.S. Pat. No. 5,877,369, EP-A-0 117146, DE-A-199 37 196, DE-A-199 37 105, U.S. Pat. No. 3,670,044, U.S. Pat. No. 6,566,573, U.S. Pat. No. 4,788,371, WO-A-94/29021 or DE-A-199 37 107. Particular preference is given in accordance with the invention to dehydrogenation catalyst materials based on platinum or on platinum-tin, which can be applied to suitable support materials, for example the preferably open-cell, preferably metallic or ceramic, foam bodies.

For heterogeneously catalyzed dehydrogenation of propane or isobutene in process step i), all reactor types and process variants known in the prior art are additionally useful. One comparatively detailed description of for suitable dehydrogenation processes is contained in Catalytica® Studies Division, "*Oxidative Dehydrogenation and Alternative Dehydrogenation Processes*", Study Number 4192 OD, 1993, 430 Ferguson Drive, Mountain View, Calif., 94043-5272 U.S.A.

In process step ii) of the process according to the invention, a gas mixture at least comprising oxygen and at least one unsaturated hydrocarbon is provided, this unsaturated hydrocarbon preferably being propene or isobutene. In addition to the unsaturated hydrocarbon and the oxygen, this gas mixture may further comprise inert gases, for example nitrogen, and steam. The exact composition of such starting gas mixtures used in the catalytic gas phase oxidation of propene or isobutene is sufficiently well known to those skilled in the art from the prior art. In the case of use of propene as the unsaturated starting material, reference is made, for example, to WO-A-03/051809, in which the exact composition of a propene-comprising gas mixture which can be supplied in a two-stage oxidation reaction is described.

In process step iii) of the process according to the invention, the unsaturated hydrocarbon obtained in process step i) or provided in process step ii) is oxidized in the gas phase to obtain a gas mixture comprising an unsaturated aldehyde in a first oxidation reactor having a first oxidation catalyst material, while, if appropriate, in process step iv) of the process according to the invention, the unsaturated aldehyde obtained in process step iii) is oxidized in the gas phase to obtain a gas mixture comprising an unsaturated carboxylic acid in a second oxidation reactor having a second oxidation catalyst material. The catalyst materials used advantageously for this purpose in the individual reaction stages and the advantageous pressure and temperature conditions can likewise be taken from WO-A-03/051809 in the case of the two-stage conversion of propene to acrylic acid. Further suitable catalyst materials, especially for the conversion of propene to acrolein and of acrolein to acrylic acid, and also the preferred pressure and temperature conditions for these reactions, can additionally also be taken from WO-A-2006/002708.

It is particularly preferred that the catalyst material used for the catalytic oxidation reaction of propene to give acrolein comprises Mo-based catalyst materials, even more preferably Mo—Bi-based catalyst materials, and Mo—Fe—Bi-based catalyst materials are the most preferred. Useful secondary components of such catalyst systems additionally include especially Co/Ni, Sb, alkali metals, alkaline earth metals, Zn, Sn, As, Pb, Pd and various other metals, usually transition metals. In addition, these catalyst materials may, for example, also be doped with inert additives to regulate the catalyst activity, in which case, for example, $Al_2O_3$, $SiO_2$, $ZrO_2$, $TiO_2$ and mixtures or compounds thereof can be employed here. For the catalytic oxidation of isobutane to methacrolein, preference is likewise given to using the above-described catalyst materials.

In the stage of the catalytic oxidation reaction of acrolein to give acrylic acid, particular preference is given to using Mo-based catalyst materials, even more preferably Mo—V-based catalyst materials, and Mo—Cu—V-based or Mo—W—V-based catalyst materials are the most preferred here. In addition, it is preferred that the catalyst materials are of the mixed oxide type. Useful secondary components of these catalyst systems include especially further transition metals. In addition, these catalyst materials too may, for example, be doped with inert additives to regulate the catalyst activity, in which case it is likewise possible here to use $Al_2O_3$, $SiO_2$, $ZrO_2$, $TiO_2$ and mixtures or compounds thereof. For the catalytic oxidation of methacrolein to methacrylic acid, preference is given to using, in addition to the above-described catalyst materials, also Mo—V—P-based catalyst materials.

When, as described at the outset, the propane or the isobutane is converted by a direct oxidation to acrylic acid or to methacrylic acid, the catalyst materials used may be those of the composition Mo—V—Te-(secondary components)-O, where the secondary components used may be especially Nb. These catalyst materials too may, for example, be doped with inert additives to regulate the catalyst activity, in which case it is possible here, for example, to employ $Al_2O_3$, $SiO_2$, $ZrO_2$, $TiO_2$ and mixtures or compounds thereof.

The space velocity of unsaturated hydrocarbon, preferably the propene or isobutene space velocity, in the process according to the invention (i.e. the amount of unsaturated hydrocarbon, preferably of propene or isobutene, in liters, which is introduced into the first oxidation reactor per liter of reactor volume and per hour) is preferably at least 150/h, more preferably at least 200/h, further preferably at least 250/h and most preferably at least 300/h.

In the process according to the invention, at least one of the reactors selected from the dehydrogenation reactor (in which the saturated hydrocarbon, preferably the propane or the isobutane, is converted to the unsaturated hydrocarbon, preferably to propene or isobutene), the first oxidation reactor (in which the unsaturated hydrocarbon, preferably the propene or the isobutene, is converted to the unsaturated aldehyde, preferably to acrolein or methacrolein), the second oxidation reactor (in which the unsaturated aldehyde, preferably the acrolein or methacrolein, is converted to the unsaturated carboxylic acid, preferably to acrylic acid or methacrylic acid) or the reactor for direct oxidation (in which the saturated hydrocarbon, preferably the propane or the isobutane, is converted to the unsaturated carboxylic acid, preferably to acrylic acid or methacrylic acid) comprises at least one preferably open-cell, preferably metallic or ceramic, foam body.

According to the invention, the following variants of the process according to the invention are conceivable:
- only the dehydrogenation reactor comprises a preferably open-cell, preferably metallic or ceramic, foam body;
- only the first oxidation reactor comprises a preferably open-cell, preferably metallic or ceramic, foam body;
- only the second oxidation reactor comprises a preferably open-cell, preferably metallic or ceramic, foam body;
- the dehydrogenation reactor and the first oxidation reactor comprise a preferably open-cell, preferably metallic or ceramic, foam body;
- the dehydrogenation reactor and the second oxidation reactor comprise a preferably open-cell, preferably metallic or ceramic, foam body;
- the first oxidation reactor and the second oxidation reactor comprise a preferably open-cell, preferably metallic or ceramic, foam body;
- the dehydrogenation reactor, the first oxidation reactor and the second oxidation reactor comprise a preferably open-cell, preferably metallic or ceramic, foam body;
- the reactor for direct oxidation comprises a preferably open-cell, preferably metallic or ceramic, foam body.

Useful preferably open-cell, metallic or ceramic foam bodies include all preferably open-cell, metallic or ceramic foam bodies which are known to those skilled in the art and can be used under the pressure and temperature conditions in the dehydrogenation reactor and/or in the first oxidation reactor and/or in the second oxidation reactor.

Useful preferably open-cell metallic foams include, for example, aluminum foams or foams composed of steel, stainless steel or copper. The production of such sponges from metals is described, for example, in U.S. Pat. No. 3,087,807 or in DE-A-40 18 360. The preferably open-cell ceramic foams too preferably consist of a three-dimensionally networked ceramic structure composed of many ceramic cell walls joined to one another and open cells between the cell walls. The type of ceramic from which the cell walls are formed can be varied and determines essential properties of the foam. Preferred open-cell foam ceramics are produced principally by molding methods, in which a preferably open-cell framework structure, for example composed of polymer foam or carbon foam, is coated with ceramic and the original substrate is removed either during or after the ceramic formation. Such a process is described, for example, in U.S. Pat. No. 3,090,094. The ceramic foam bodies are preferably based on mixed oxides or carbides. The materials used for ceramic foam bodies usable in accordance with the invention are, for example, materials such as cordient, steatite, Duranit®, silicon carbide for oxidically bound silicon carbide, or foam bodies composed of silicon dioxide, aluminum oxides, aluminosilicates or aluminates. One example of a process for producing a preferably open-cell, silicon carbide-based, ceramic foam is the process described in WO-A-02/020426. It is additionally preferred in accordance with the invention that the metallic or ceramic foam bodies have a cell width within a range from 1 to 90 ppi ("pores per inch"), more preferably within a range from 5 to 80 ppi and most preferably within a range from 10 to 40 ppi.

In one embodiment of the process according to the invention, the preferably open-cell, preferably metallic or ceramic foam bodies are not coated with the dehydrogenation catalyst material, the first oxidation catalyst material or the second oxidation catalyst material, but are present in the particular reactors in addition to corresponding fixed beds.

In a preferred embodiment of the process according to the invention, however, at least part of the surface of the preferably open-cell, preferably metallic or ceramic foam body is covered with the dehydrogenation catalyst material, the first oxidation catalyst material, the second oxidation catalyst material (according to whether the foam body is present in the dehydrogenation reactor, in the first oxidation reactor or in the second oxidation reactor), or the catalyst material suitable for performance of a direct oxidation. The preferably open-cell, metallic or ceramic foam body serves in this case as a support material for the catalyst material used in the particular reactor (dehydrogenation reactor, first oxidation reactor or second oxidation reactor). In addition, however, another conceivable embodiment is one in which the preferably open-cell foam body itself consists of a material with corresponding catalytic activity, by virtue, for example, of it having been formed therefrom.

The preferably open-cell, preferably metallic or ceramic foam body is coated with the dehydrogenation catalyst, the first oxidation catalyst or the second oxidation catalyst (i.e., for example, with the Mo-based catalyst material, more preferably the Mo—Bi-based catalyst material and most preferably with the Mo—Fe—Bi-based catalyst material of the first oxidation stage or with the Mo-based catalyst material, more preferably the Mo—V-based catalyst material and most preferably with the Mo—Cu—V-based, Mo—W—V-based or Mo—V—P-based catalyst material of the second oxidation stage) preferably by applying a solution or a suspension of the catalyst material to the surface of its inner cavities, followed by drying with subsequent calcination at higher temperatures for solidification and final surface configuration of the catalyst material applied.

In a preferred embodiment of the process according to the invention for preparing unsaturated aldehydes or unsaturated carboxylic acids, the preferably open-cell, preferably metallic or ceramic foam body covered at least partly by the catalyst is accordingly obtainable by a process comprising the process steps of:

A1) preparing a solution or a suspension composed of the preferably pulverulent catalyst material, a solvent or a solvent mixture and optionally further additives;

A2) contacting at least part of the surface of the preferably open-cell, preferably metallic or ceramic foam body with the solution or the suspension;

A3) if appropriate discharging an excess of solution or suspension;

A4) if appropriate drying the preferably open-cell, preferably metallic or ceramic foam body;

A5) calcining the catalyst material.

In process step A1), a solution or suspension of the preferably pulverulent catalyst material in a suitable solvent or solvent mixture, for example water, mono- or polyhydric alcohols or mixtures thereof is first prepared, optionally with addition of additives, such as inorganic or organic binders, surfactants, catalytic active components, pore formers, rheology aids, inert materials for regulating the catalyst activity, adhesion promoters, defoamers, dispersing aids and other additives. In process step A2), at least part of the surface of the preferably open-cell, preferably metallic or ceramic foam body is then contacted with the solution or suspension. This can be done, for example, by filling the foam body with the solution or suspension by a dipping, suction, painting or pumping process. The prior art describes processes in which only the exactly calculated amount of solution or suspension which is to remain in the foam body is introduced into the foam body and this amount is distributed very homogeneously on the outer and inner surfaces of the foam body. Other processes introduce an excess into the foam body (e.g. flooding of the foam body) and perform a subsequent emptying operation, with which excess solution or suspension is discharged in process step A3). Often, emptying is performed by blowing out by means of an air stream, emptying also being possible by means of rotation of the foam body or by suction. In process step A4), the preferably open-cell, preferably metallic or ceramic foam body is then dried, this drying being effected preferably at temperatures in a range from 50 to 200° C., more preferably in a range from 100 to 150° C. It is conceivable to perform process steps A1) to A3), especially also process steps A1) to A4), repeatedly in succession, in order to be able in this way, for example, to vary the thickness of the layer applied on the catalyst material.

In process step A5), the catalyst material present on the surface of the foam body is then calcined, this calcining being effected preferably by heating the foam body covered with the catalyst material to temperatures in a range from 250 to 750° C., more preferably in a range from 300 to 600° C. and most preferably in a range from 350 to 500° C. Preference is given to effecting the calcining by passing a gas stream through, for example $N_2$ and/or air.

In a further particular embodiment of the process according to the invention, at least one of the reactors selected from the dehydrogenation reactor, the first oxidation reactor, the second oxidation reactor or that reactor in which a direct oxidation is performed is a tube bundle reactor comprising at least two reaction tubes, and the dehydrogenation catalyst material, the first oxidation catalyst material, the second oxidation catalyst material or the material which catalyses the direct oxidation and the preferably open-cell foam body or the preferably open-cell foam body coated with the dehydrogenation catalyst material, the first oxidation catalyst material, the second oxidation catalyst material or the material which catalyses the direct oxidation, or the preferably open-cell foam body shaped from the dehydrogenation catalyst material, the first oxidation catalyst material, the second oxidation catalyst material or the material which catalyses the direct oxidation, is/are localized in the interior of the reaction tubes. Such tube bundle reactors comprise a tube bundle which is formed from a multitude of parallel reactor tubes and is arranged in the reactor shell. The open ends of the reactor tubes are secured with sealing in upper and lower tube plates and open into an upper and lower reactor hood in each case. Through the reactor hoods, the reactant is supplied and the product mixture leaving the reactor tubes is removed. In a particular embodiment of the process according to the invention, at least two, three, four, five or even more tube bundle reactors of this type can be operated in parallel to one another.

In the space between the upper and lower tube plates, which may be divided by deflecting plates, a heat carrier circulates, and can be conducted in cocurrent, countercurrent or crosscurrent. Corresponding inlets and outlets for the heat carrier medium are arranged in the reactor shell, through which the heat carrier medium is conducted in circulation by means of pumps, and wherein a target temperature is established by means of external heat exchangers. The reactor shell can be divided into two or more independent temperature control zones, each of which is operated with independently circulating heat carrier media. The individual zones are separated from one another by tube plates which are arranged horizontally in the tube bundle reactor and through which the reactor tubes are conducted.

The individual tubes of the tube bundle reactor preferably have a diameter of more than 3 cm, more preferably more than 5 cm and even more preferably more than 10 cm.

Moreover, in addition to the above-described particular embodiment of the process according to the invention, it is also conceivable to use wall reactors or plate reactors. In wall reactors, a reaction mixture is passed through between two catalytically coated plate-shaped wall elements arranged in parallel in each case, the catalyst material (dehydrogenation catalyst material, first oxidation catalyst material, second oxidation catalyst material or material which catalyses the direct oxidation) and the foam body, the foam body coated with the catalyst material or that formed from this catalyst material being localized between two adjacent plates. Typically, such a reactor consists of a series of wall elements. Owing to the small wall element separation, a high wall to volume ratio is achieved, which allows a high heat removal rate and a mode of operation with reaction mixtures which are explosive under normal conditions. The high removal rate enables very good temperature control with avoidance of "hotspots" in strongly exothermic reactions. Wall reactors can therefore be operated at a higher temperature level than in polytropic mode. As a result of this, higher space-time yields can be achieved in catalytic wall reactors. The good heat transfer also allows particularly active catalyst materials to be used, whose evolution of heat cannot be controlled in conventional reactors.

Moreover, it is possible in principle that the particular catalyst material (dehydrogenation catalyst material, first oxidation catalyst material, second oxidation catalyst material or catalyst material which catalyses a direct oxidation) in the particular reactors is applied both to the surfaces of the reactor (in the case of a tube bundle reactor to the inner faces of the reaction tubes and in the case of a wall reactor in typically to the plate-shaped wall elements) and to the surfaces of the preferably open-cell, metallic or ceramic foam body.

Moreover, it is preferred in a particular variant of the process according to the invention that, in at least one of the reactors selected from the dehydrogenation reactor, the first oxidation reactor, the second oxidation reactor or that reactor in which a direct oxidation is performed, but preferably in the first oxidation reactor, the second oxidation reactor or the first and the second oxidation reactor, at least two separable metallic or ceramic foam bodies coated with the catalyst material, or foam bodies formed from the catalyst material, are present. The foam bodies may, for example, be present in the form of random packings which have, for instance, the shape of spheres or rings, whose size ratios are preferably designed so as to achieve a very tight packing. Such random packings are preferably characterized in that they have a diameter which is at most 50%, more preferably at most 40% and most preferably at most 30%, but preferably at least 5% and even more preferably at least 10%, of the diameter of the reactor (in the case of a tube bundle reactor, of the diameter of the particular reaction tubes, and, in the case of a wall reactor, of the distance between two adjacent plates). In addition to a random packing form, the foam bodies can also be used in the form of blocks, for example in the form of cylinders, if appropriate also hollow cylinders. Such blocks are preferably characterized in that they have a diameter which is at least 50%, more preferably at least 75%, even more preferably at least 90% and most preferably at least 95% of the diameter of the reactor (in the case of a tube bundle reactor, of the diameter of the particular reaction tubes, and, in the case of a wall reactor, of the distance between two adjacent plates).

The number of separable foam bodies present in the reactors depends on the shape of these foam bodies. In a first particular embodiment of the process according to the invention, in which the foam bodies are introduced into the reactor or the reaction tubes of the tube bundle reactor as random packings in the form of a fixed bed, preferably 500 to 20 000, more preferably 1000 to 15 000 and most preferably 2000 to 10 000 separable foam bodies preferably coated with catalyst material or formed from catalyst material are used per reactor. In a second particular embodiment of the process according to the invention, in which the foam bodies are introduced into the reactor or the reaction tubes of the tube bundle reactor not in the form of a fixed bed but in the form of foam body blocks, preferably 1 to 500, more preferably 2 to 100 and most preferably 3 to 50 separable foam body blocks preferably coated with catalyst material or formed from catalyst material are used per reactor.

In connection with the above-described particular variant of the process according to the invention, it may additionally be found to be advantageous when the at least two separable foam bodies of a reactor which are coated with the particular catalyst material or formed from the catalyst material differ by their catalyst activity, reported in the activity per unit volume of the catalyst. In this case, especially in the dehydrogenation reactor, in the first oxidation reactor, in the second oxidation reactor, in the dehydrogenation reactor and in the first oxidation reactor, in the dehydrogenation reactor and in the second oxidation reactor, in the first oxidation reactor and in the second oxidation reactor, in the dehydrogenation reactor and in the first and second oxidation reactors, or in that reactor in which a direct oxidation is performed, it may be found to be advantageous when the at least two separable foam bodies coated with the catalyst material or formed from the catalyst material are arranged within the reactor such that the catalytic activity per volume element of the reactor increases in the direction from the reactant inlet (i.e. from the inlet of the saturated hydrocarbon in the case of the dehydrogenation reactor or of the reactor used for direct oxidation, from the inlet of the unsaturated hydrocarbon in the case of the first oxidation reactor, or from the inlet of the unsaturated aldehyde in the case of the second oxidation reactor) to the product outlet (i.e. to the outlet for the unsaturated hydrocarbon in the case of the dehydrogenation reactor or for the unsaturated carboxylic acid in the case of a reactor used for direct oxidation, to the outlet for the unsaturated aldehyde in the case of the first oxidation reactor or to the outlet of the unsaturated carboxylic acid in the case of the second oxidation reactor).

The variation in the catalyst activity of the particular foam bodies within a reactor can be achieved, for example, by the following measures, which may optionally also be combined with one another: adjustment of the catalyst density and/or of the catalyst mass in the individual foam bodies (for example through the use of foam bodies with different ppi number), selection of catalyst materials of different activity, different doping of the catalyst material with inert substances, application of the catalyst material in different density and/or mass (by preparing, in process step A1), suspensions with different concentration with regard to the catalyst material, or, for example, performing process steps A1) to A3), especially also process steps A1) to A4), repeatedly in succession).

In addition, it may be advantageous in accordance with the invention, in the particular reactors, to combine preferably open-cell foam bodies coated with the catalyst material or formed from the catalyst material, or else preferably open-cell foam bodies formed from catalyst material, with conventional fixed beds (i.e. catalysts which do not comprise any preferably open-cell foam bodies). Such conventional fixed beds may consist, for example, of to random packings, for example spheres or rings, shaped catalyst materials or of catalytically inactive random packings which are coated in the with the catalyst material. Such a combination can be achieved within one reaction tube of a tube bundle reactor or within one plate interstice of a wall reactor, or, for example, by virtue of two reactors, for example two tube bundle reactors or two wall reactors, being arranged in series, in which case, for example, the preferably open-cell foam body coated with the catalyst or formed from the catalyst is provided in the first reactor, and a conventional fixed catalyst bed in the second reactor.

In this connection, it is especially preferred that, in the case of a reactor with length L, where the point $L_0$ is the reactant inlet and the point $L_{max}$ is the product outlet of the reactor, the preferably open-cell foam body coated with the catalyst material or else the preferably open-cell foam body formed from catalyst material is introduced into a region of the reactor (in the case of a tube bundle reactor, into a region of each reaction tube, and, in the case of a wall reactor, into a region between two adjacent plates in each case), which ranges from $L_0$ to at most $0.9 \times L_{max}$, more preferably from $L_0$ to at most $0.8 \times L_{max}$ and most preferably from $L_0$ to at most $0.7 \times L_{max}$, and the conventional fixed beds are introduced into a region of each reaction tube (in the case of a tube bundle reactor, into a region of each reaction tube, and, in the case of a wall reactor, into a region between two adjacent plates in each case), which ranges from at least $0.5 \times L_{max}$ to $L_{max}$, more preferably at least $0.6 \times L_{max}$ to $L_{max}$ and most preferably from at least $0.7 \times L_{max}$ to $L_{max}$.

The foam bodies are accordingly more preferably introduced in the region of the front ⅔ of the reactor, followed by a conventional fixed bed.

A further contribution to the achievement of the objects stated at the outset is made by a process for preparing purified unsaturated carboxylic acids, preferably for preparing acrylic acid or methacrylic acid, comprising the process steps of:

(I) preparing a gas mixture comprising an unsaturated carboxylic acid, preferably acrylic acid or methacrylic acid, by the above-described process according to the invention for preparing unsaturated carboxylic acids;
(II) absorbing the unsaturated carboxylic acid, preferably the acrylic acid or the methacrylic acid, in a solvent to obtain a solution comprising an unsaturated carboxylic acid, preferably acrylic acid or methacrylic acid;
(III) removing the unsaturated carboxylic acid, preferably the acrylic acid or the methacrylic acid, from the solution comprising the unsaturated carboxylic acid, preferably the acrylic acid or the methacrylic acid, by means of distillation, extraction, crystallization or a combination of these removal methods.

Useful solvents in process step II) include water or an organic compound with a boiling point in a range from 50 to 250° C., preferably in a range from 70 to 180° C. and further preferably in a range from 105 to 150° C., or water and this organic compound. Useful organic compounds of this kind include especially aromatics and further preferably alkylated aromatics. Typically, the solvent which acts as the quenching agent is contacted with the monomer gas in a suitable column, preferably in countercurrent.

It is especially preferred in this connection that the solution obtained in process step II) (the quench phase) comprises the unsaturated carboxylic acid, preferably the acrylic acid or the methacrylic acid, in an amount in a range from 30 to 90% by weight, preferably in a range from 35 to 85% by weight and further preferably in a range from 45 to 75% by weight, based in each case on the quench phase. It is additionally preferred that the quench phase is worked up at temperatures below the boiling point of the unsaturated carboxylic acid. In the case of acrylic acid, a measure suitable for this purpose consists in using a correspondingly cold quenching agent with a temperature of less than 40° C. The quench phase at such a temperature can then be sent to an extraction or crystallization or both for workup in process step III), the temperatures in the case of acrylic acid being preferably in a range from −40 to 40° C., preferably in a range from −20 to 39° C. and more preferably in a range from −10 to 35° C.

In process step III), the quench phase is then worked up. In the case that the quenching agent consists of water to an extent of at least 50% by weight, preferably at least 70% by weight, it is preferred that the aqueous quenching agent burdened with the unsaturated carboxylic acid, for example with acrylic acid, is worked up in a further step with a separating agent which preferably does not have good water solubility. The most carboxylic acid-rich phase is subjected either to a distillation or to a crystallization, or to both, preferably first to a crystallization. The crystallization can be performed either as a layer crystallization or as a suspension crystallization. Suitable layer crystallization apparatus is obtained commercially from Sulzer AG. Suitable suspension crystallization methods generally make use of a crystal generator followed by a wash column. Such apparatus and methods are commercially obtainable from Niro Prozesstechnologie BV. A useful extractant/separating agent in the case of acrylic acid as the unsaturated carboxylic acid is especially an aromatic compound, further preferably an alkylaromatic and more preferably toluene. If an organic compound is to be used as the separating agent, this organic compound burdened with acrylic acid may likewise be subjected either to a distillation or to a crystallization, or to a combination of the two. A crystallization suitable for this purpose is disclosed in EP-A-1 015 410.

A further contribution to achieving the objects stated at the outset is made by a process for preparing a polymer based on unsaturated carboxylic acids, preferably on acrylic acid or methacrylic acid, comprising the process steps of:
(α1) preparing a purified unsaturated hydrocarbon, preferably acrylic acid or methacrylic acid, by the process described above;
(α2) free-radically polymerizing the unsaturated hydrocarbon, preferably the acrylic acid or the methacrylic acid.

This free-radical polymerization in process step (α2) is preferably effected in the form of an aqueous solution polymerization or of an emulsion or suspension polymerization, in which the unsaturated hydrocarbon is preferably free-radically polymerized in preferably partly neutralized form in the presence of crosslinkers to obtain a polymer gel. The polymer gel thus obtained is subsequently, if it was obtained by solution polymerization, comminuted and then dried. In the case of use of acrylic acid as the unsaturated carboxylic acid, it is possible in this way to obtain water-absorbing polymer structures which are suitable especially as superabsorbents for use in hygiene articles, for example nappies. Further details of the production of such water-absorbent polymer structures by free-radical polymerization of acrylic acid can be found, among other sources, in the 3rd chapter in "*Modern Superabsorbent Polymer Technology*", F. L. Buchholz and A. T. Graham (Editors), Wiley-VCH, New York, 1998.

A further contribution to the achievement of the problems stated at the outset is made by an apparatus for preparing the purified, unsaturated carboxylic acids, preferably acrylic acid or methacrylic acid, comprising, as apparatus constituents:
(β1) if appropriate a reactor for direct oxidation of saturated hydrocarbons, having a catalyst material which catalyses the conversion of saturated hydrocarbons to unsaturated carboxylic acids;
(β2) if appropriate a dehydrogenation reactor having a dehydrogenation catalyst material;
(β3) if appropriate a first oxidation reactor, if appropriate with a fluid connection to the dehydrogenation reactor (β2), having a first oxidation catalyst material;
(β4) if appropriate a second oxidation reactor with a fluid connection to the first oxidation reactor (β3), having a second oxidation catalyst material;
(β5) a quench apparatus with a fluid connection to the second oxidation reactor (β1) or (β3);
(β6) a purification unit with a fluid connection to the quench apparatus (β5);
wherein at least one of the reactors selected from the reactor for direct oxidation (β1), the dehydrogenation reactor (β2), the first oxidation reactor (β3) and the second oxidation reactor (β4), preferably the first oxidation reactor (β3), the second oxidation reactor (β4) or the first and second oxidation reactors (β3) and (β4), comprises at least one preferably open-cell, preferably metallic or ceramic, foam body.

Useful dehydrogenation or first or second oxidation catalyst materials, useful catalyst materials for a direct oxidation, and useful dehydrogenation or first or second oxidation reactors and useful reactors for a direct oxidation are in principle those catalyst materials or reactors which have already been mentioned as preferred catalyst materials and reactors at the outset in connection with the process according to the invention for preparing an unsaturated carboxylic acid. Preferred open-cell, metallic or ceramic foam bodies are in principle likewise those preferably open-cell bodies which were mentioned as preferred preferably open-cell foam bodies at the outset in connection with the process according to the invention for preparing an unsaturated carboxylic acid.

In connection with the inventive apparatus too, it is particularly preferred that at least part of the surface of the preferably open-cell, metallic or ceramic foam body is coated with the dehydrogenation catalyst material, with the first or second oxidation catalyst material or the catalyst material for a direct oxidation. This preferably open-cell foam body coated with the catalyst material is preferably obtainable by the coating process described at the outset, comprising process steps A1) to A5).

In a particular embodiment of the inventive apparatus, at least one of the reactors selected from reactor for direct oxidation ($\beta 1$), the dehydrogenation reactor ($\beta 2$), the first oxidation reactor ($\beta 3$) and the second oxidation reactor ($\beta 4$), but preferably the first oxidation reactor ($\beta 3$), the second oxidation reactor ($\beta 4$) or the first and second oxidation reactors ($\beta 3$) and ($\beta 4$), is/are a tube bundle reactor comprising at least two reaction tubes, and the dehydrogenation catalyst material, the first or second oxidation catalyst material or the catalyst material for direct oxidation and the preferably open-cell foam body or the preferably open-cell foam body coated with the dehydrogenation catalyst material, the first or the second oxidation catalyst material or the catalyst material for direct oxidation is/are localized in the interior of the reaction tubes.

It may also be advantageous in connection with the inventive apparatus when at least one of the reactors selected from the reactor for direct oxidation ($\beta 1$), the dehydrogenation reactor ($\beta 2$), the first oxidation reactor ($\beta 3$) and the second oxidation reactor ($\beta 4$), but preferably the first oxidation reactor ($\beta 3$), the second oxidation reactor ($\beta 4$) or the first and second oxidation reactors ($\beta 3$) and ($\beta 4$) have at least two separable, preferably open-cell foam bodies coated with the catalyst material, and at least two foam bodies of a reactor, as already specified in connection with the process according to the invention for preparing unsaturated aldehydes or unsaturated carboxylic acids, differ by their catalyst activity, reported in the activity per unit volume of the catalyst, and this different catalyst activity of the separable foam bodies can preferably be achieved by the measures described in connection with the process according to the invention for preparing unsaturated aldehydes or unsaturated carboxylic acids. In this connection, it may further be advantageous when the at least two separable foam bodies coated with the catalyst material are arranged within the reactors such that the catalytic activity per volume element increases in the direction from the reactant inlet (i.e. from the inlet of the saturated hydrocarbon in the case of the dehydrogenation reactor ($\beta 2$) or of the reactor ($\beta 1$) used for direct oxidation, from the inlet of the unsaturated hydrocarbon in the case of the first oxidation reactor ($\beta 3$) or from the inlet of the unsaturated aldehyde in the case of the second oxidation reactor ($\beta 4$) to the product outlet (i.e. to the outlet for the unsaturated hydrocarbon in the case of the dehydrogenation reactor ($\beta 2$) or for the unsaturated carboxylic acid in the case of a reactor ($\beta 1$) used for direct oxidation, to the outlet for the unsaturated aldehyde in the case of the first oxidation reactor ($\beta 3$) or to the outlet of the unsaturated carboxylic acid in the case of the second oxidation reactor ($\beta 4$).

In a particular embodiment of the inventive apparatus, it additionally comprises a polymerization unit ($\beta 7$) with a fluid connection to the purification unit ($\beta 6$).

A contribution to the achievement of the objects stated at the outset is also made by the use of the above-described apparatus in the process according to the invention for preparing unsaturated carboxylic acids, especially for preparing acrylic acid or methacrylic acid. More particularly, a contribution to the achievement of the objects stated at the outset is made by the use of the above-described apparatus additionally comprising the polymerization unit ($\beta 7$) in the above-described process according to the invention for preparing a polymer based on unsaturated carboxylic acids, preferably on acrylic acid or methacrylic acid.

The invention is now illustrated in detail with reference to nonlimiting figures and examples.

Figure 1:
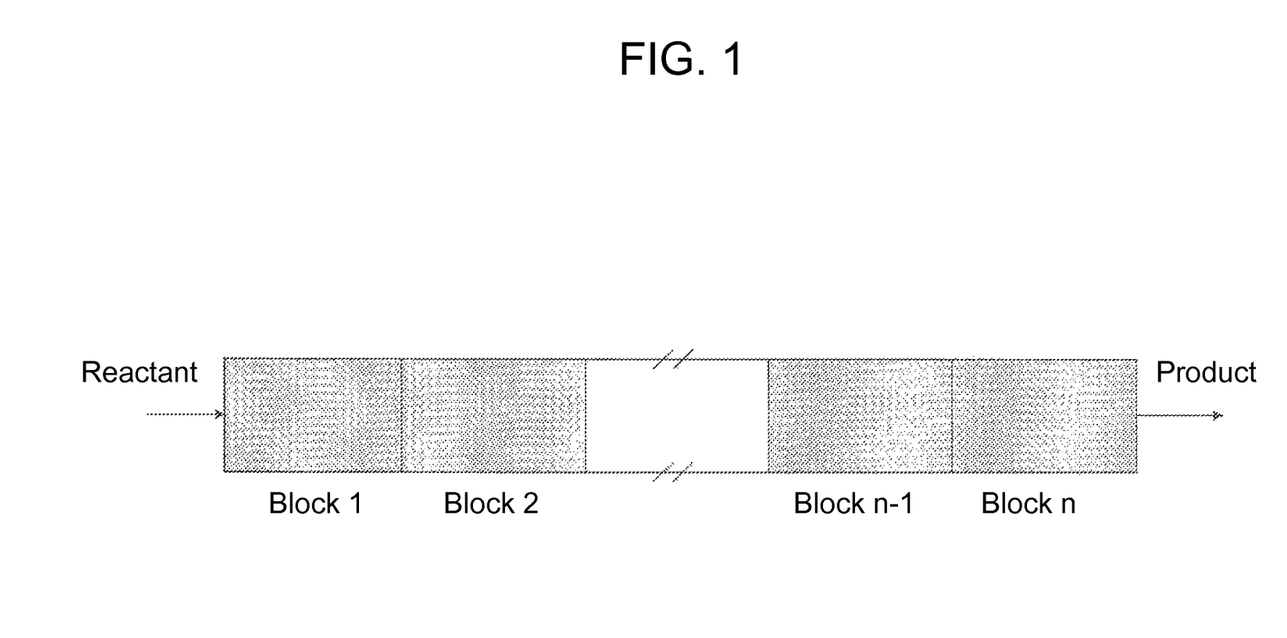
FIG. 1 is a block diagram showing foam bodies having same catalytic activity.

FIG. 1 shows, by way of example, an inventive arrangement of foam bodies coated with catalyst material in the form of separable blocks (blocks 1 to n, only the blocks 1, 2, n−1 and n being shown, where n can assume a value of up to 500) within a reactor. An individual reaction tube is shown, which may, for example, be part of a tube bundle reactor. In FIG. 1, the individual blocks 1 to n have essentially the same catalytic activity per volume element of the reactor.

Figure 2:
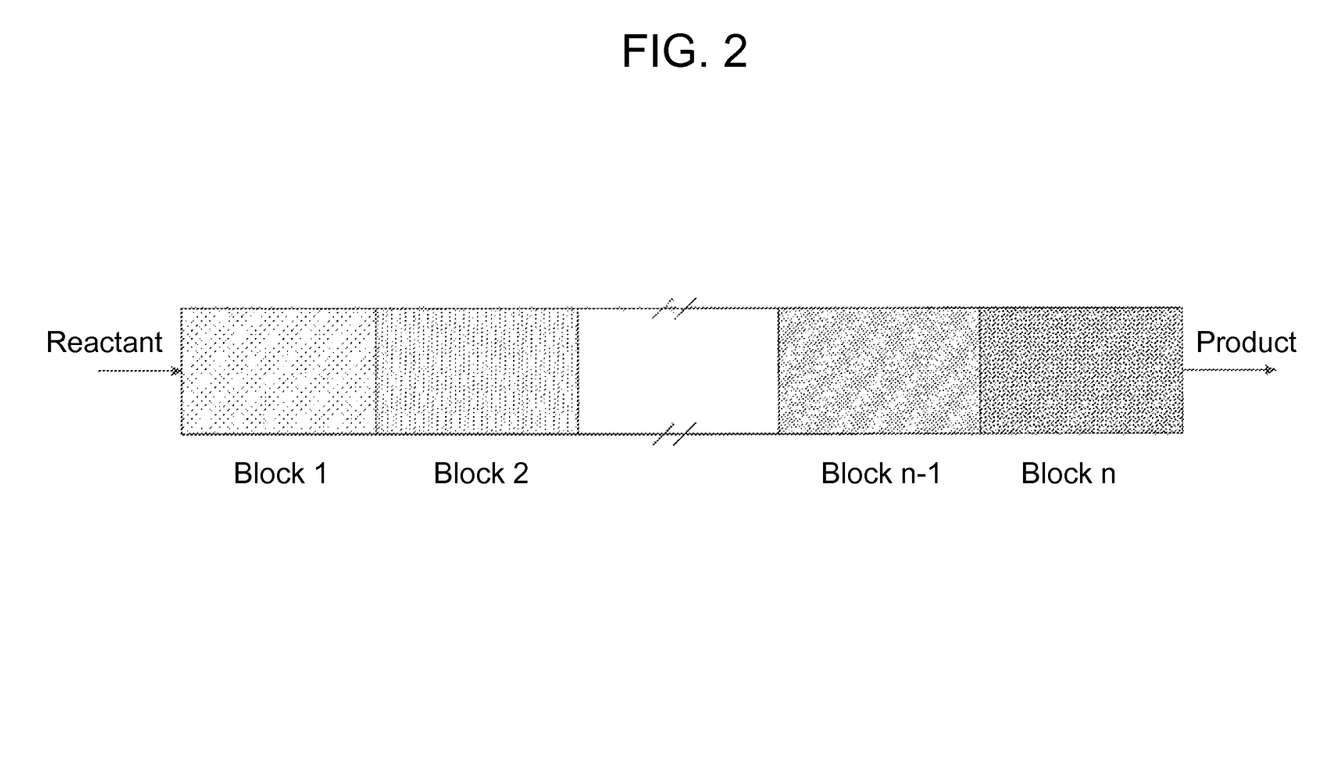
FIG. 2 is a block diagram showing foam bodies having increasing catalytic activity.

FIG. 2 likewise shows, by way of example, an inventive arrangement of foam bodies coated with catalyst material in the form of separable blocks (blocks 1 to n, again only blocks 1, 2, n−1 and n being shown, where n may assume a value of up to 500) within a reactor. In contrast to FIG. 1, the catalytic activity per volume element of the reactor increases in the direction from the reactant inlet to the product outlet (indicated by the increasing dot density within the blocks 1 to n in FIG. 2).

Figure 3:
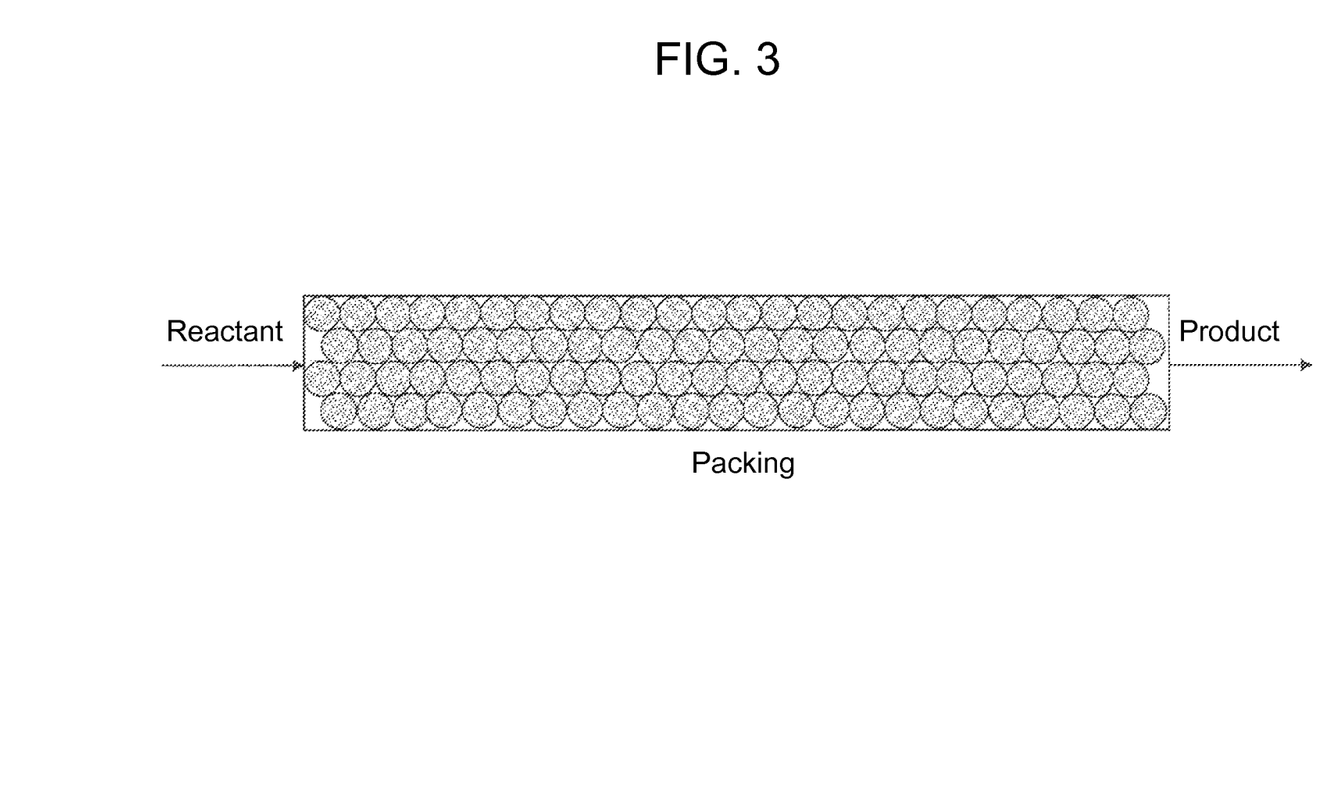
FIG. 3 is a diagram showing random packing of spherical foam bodies.

FIG. 3 shows, by way of example, an inventive arrangement of foam bodies coated with catalyst material in the form of a random packing bed composed of spherical foam bodies coated with the catalyst material within a reactor, the individual foam bodies having essentially the same catalytic activity per volume element.

Figure 4:
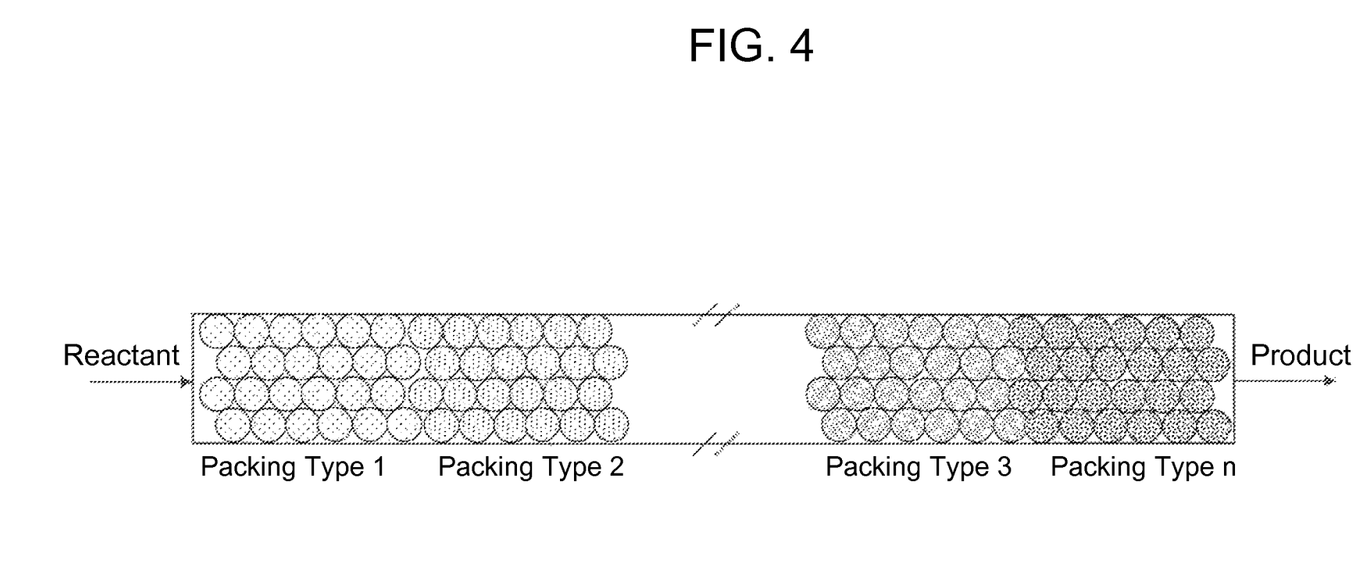
FIG. 4 is a diagram showing random packing of spherical foam bodies and increasing catalytic activity.

FIG. 4 shows, by way of example, a further inventive arrangement of foam bodies coated with catalyst material in the form of a random packing bed composed of spherical foam bodies coated with the catalyst material within a reactor, this arrangement showing foam bodies with different catalytic activity per volume element (random packing type 1 to n, only random packing types 1, 2, n−1 and n being shown, where n here too may also assume a value of up to 500). In this embodiment, the catalytic activity per volume element of the reactor increases in the direction from the reactant inlet to the product outlet (indicated by the increasing dot density within the individual spherical random packings in FIG. 4).

Figure 5:
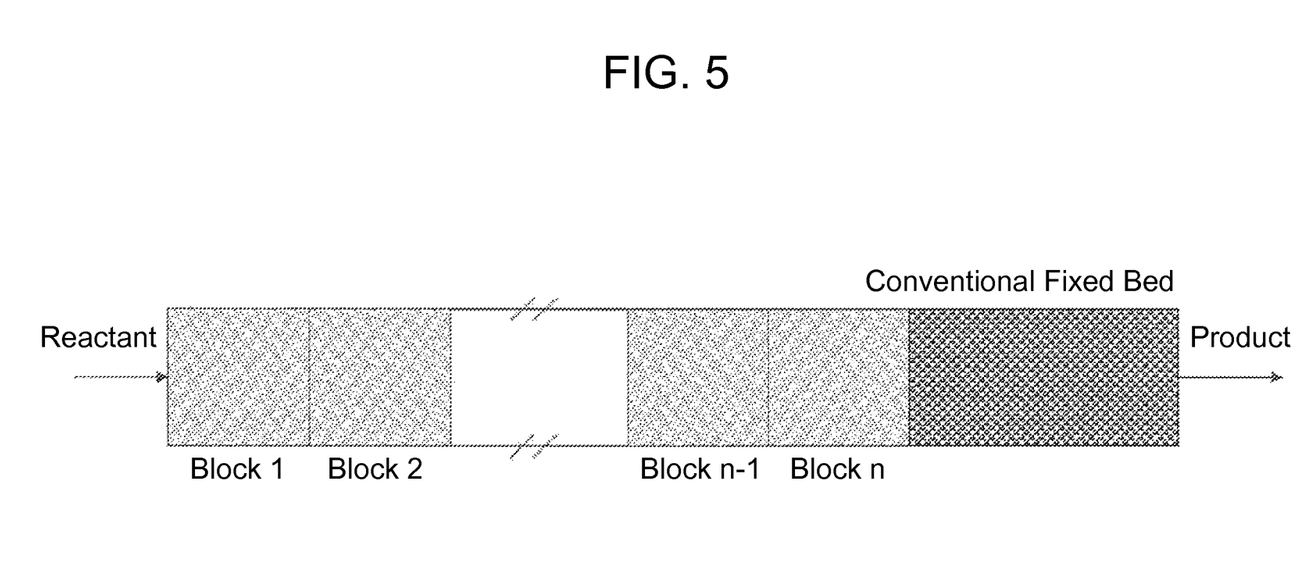
FIG. 5 is a diagram showing a combination of reaction tube and conventional fixed bed are used.

FIG. 5 shows a particular embodiment of the process according to the invention, in which, within a reactor, for example within a reaction tube of a tube bundle reactor, both foam bodies coated with catalyst material (in FIG. 5 in the form of foam body blocks 1 to n, again only blocks 1, 2, n−1 and n being shown, where n may assume a value of up to 500) and a conventional fixed bed are used. The foam body is arranged in the region of the front two thirds of the reaction tube, while the conventional fixed bed is localized in the rear third of the reactor. In this embodiment too, the catalytic activity per volume element of the reactor in the area occupied by the foam body can increase in the direction from the reactant inlet to the product outlet (not shown in FIG. 5).

Figure 6:
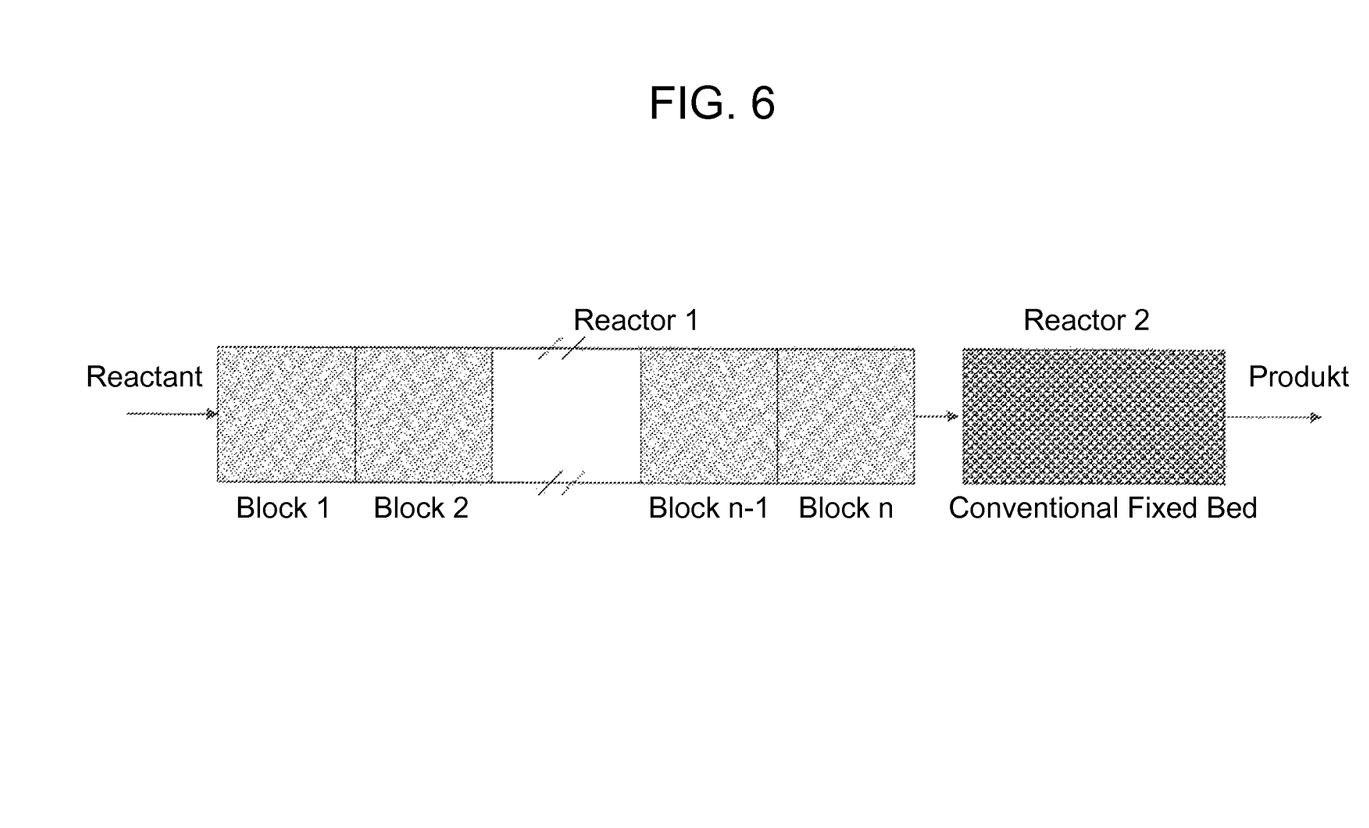
FIG. 6 is a diagram showing two reactors.

FIG. 6 shows a particular configuration of the mode of operation described in FIG. 5, wherein foam bodies coated with catalyst material (in FIG. 6 in the form of foam body blocks 1 to n, again only blocks 1, 2, n−1 and n being shown, where n may assume a value of up to 500) and a conventional fixed bed are combined with one another not within the same reactor but in the form of two reactors connected in series. In this embodiment too, the catalytic activity per volume element of the reactor in the area occupied by the foam body (reactor 1) may increase in the direction from the reactant inlet to the product outlet (not shown in FIG. 6).

EXAMPLE 4.81 g of a catalyst powder (Mo—V—W—Cu) are weighed together with 1.79 g of binder (Acti-Gel). 54 ml of water are added thereto. The components are stirred to give rise to a homogeneous suspension. The catalyst powder is prepared by the procedure described in Kunert et al., Appl. Catal., A 269 (2004), pages 53-61.

A cleaned stainless steel foam support (63.2 mm×20.0 mm; 20 ppi; mass: 13.41 g) is dip-coated in the resulting suspension, such that it is covered completely with the suspension. The duration of the coating operation is 5 minutes. Suspension and support are always moved counter to one another during this time.

After the coating operation, the sponge is freed of excess residual suspension by means of a hot air blower, and dried at 120° C. in an air stream for 180 min. This is followed by calcining at 390° C. in a calcining oven for 5 hours.

The foam body which has been coated with the catalyst material and is obtained in this way is used in a process according to Example 1 of WO-A-03/051809 in the first and second oxidation stages for preparation of acrylic acid from propene.

It is found that, compared to a conventional fixed bed, the temperature difference between the heat transfer medium and the catalyst material was significantly lower.

The invention claimed is:

1. A process for preparing unsaturated aldehydes or unsaturated carboxylic acids by heterogeneous catalytic gas phase oxidation of unsaturated or saturated hydrocarbons, comprising the process steps of:
   i) providing a gas mixture at least comprising a saturated hydrocarbon and catalytically dehydrogenating the at least one saturated hydrocarbon in the gas phase to obtain a gas mixture comprising an unsaturated hydrocarbon in a dehydrogenation reactor having a dehydrogenation catalyst material; or
   ii) providing a gas mixture at least comprising oxygen and at least one unsaturated hydrocarbon wherein unsaturated hydrocarbon has a space velocity of at least 150 liters/hr;
   iii) catalytically oxidizing the unsaturated hydrocarbon obtained in process step i) or provided in process step ii) in the gas phase to obtain a gas mixture comprising an unsaturated aldehyde in a first oxidation reactor having a first oxidation catalyst material;
   iv) catalytically oxidizing the unsaturated aldehyde obtained in process step iii) in the gas phase to obtain a gas mixture comprising an unsaturated carboxylic acid in a second oxidation reactor having a second oxidation catalyst material;
   wherein at least one of the reactors selected from the dehydrogenation reactor, the first oxidation reactor and the second oxidation reactor comprises at least one open-cell foam body and the foam body is characterized by a cell width within a range of from 10 to 40 ppi, and wherein the foam bodies are present in the form of random packings, such random packings are characterized in that they have a diameter which is at most 50% and at least 5% of the diameter of the reactor, in the case of a tube bundle reactor, of the diameter of the particular reaction tubes, and, in the case of a wall reactor, of the distance between two adjacent plates, or in the form of blocks, such blocks are characterized in that they have a diameter which is at least 90% of the diameter of the reactor, in the case of a tube bundle reactor, of the diameter of the particular reaction tubes, and, in the case of a wall reactor, of the distance between two adjacent plates.

2. The process according to claim 1, wherein the process comprises process steps ii), iii) and iv), and the unsaturated hydrocarbon is propene, the unsaturated aldehyde acrolein and the unsaturated carboxylic acid acrylic acid.

3. The process according to claim 1, wherein the process comprises process steps ii), iii) and iv), and the unsaturated hydrocarbon is isobutene, the unsaturated aldehyde methacrolein and the unsaturated carboxylic acid methacrylic acid.

4. The process according to claim 1, wherein the process comprises process steps i), ii), iii) and iv), and the saturated hydrocarbon is propane, the unsaturated hydrocarbon propene, the unsaturated aldehyde acrolein and the unsaturated carboxylic acid acrylic acid.

5. The process according to claim 1, wherein the process comprises process steps i), ii), iii) and iv), and the saturated hydrocarbon is isobutane, the unsaturated hydrocarbon isobutene, the unsaturated aldehyde methacrolein and the unsaturated carboxylic acid methacrylic acid.

6. The process according to claim 1, wherein unsaturated hydrocarbon has a space velocity of at least 300 liters/hr.

7. The process according to claim 1, wherein the dehydrogenation reactor comprises the foam body.

8. The process according to claim 1, wherein the first oxidation reactor comprises the foam body.

9. The process according to claim 1, wherein the second oxidation reactor comprises the foam body.

10. The process according to claim 1, wherein the first and the second oxidation reactors comprise the foam body.

11. The process according to claim 1, wherein at least part of the surface of the open-cell foam body is coated with the dehydrogenation catalyst material, the first oxidation catalyst material, or the second oxidation catalyst material.

12. The process according to claim 10, wherein the open-cell foam body which has been coated with the catalyst material and has a cell width within a range from 10 to 40 ppi is obtainable by a process comprising the process steps of:
    A1) preparing a suspension composed of the catalyst material, a solvent or a solvent mixture and optionally further additives;
    A2) contacting at least part of the surface of the foam body with the suspension;
    A3) if appropriate discharging an excess of suspension;
    A4) if appropriate drying the foam body;
    A5) calcining the catalyst material.

13. The process according to claim 1, wherein the foam body itself is formed from a material with catalytic activity.

14. The process according to claim 1, wherein at least one of the reactors selected from the dehydrogenation reactor, the first oxidation reactor, the second oxidation reactor or a reactor for direct oxidation of saturated hydrocarbon to unsaturated carboxylic acids is a tube bundle reactor comprising at least two reaction tubes, and the dehydrogenation catalyst, the first oxidation catalyst, or the second oxidation catalyst, and the foam body or the foam body coated with the dehydrogenation catalyst, the first oxidation catalyst, or the second oxidation catalyst which catalyses the direct oxidation of a saturated hydrocarbon to an unsaturated carboxylic acid, or that formed from this catalyst material, is localized in the interior of the reaction tubes.

15. The process according to claim 14, wherein at least two tube bundle reactors are operated in parallel to one another.

16. The process according to claim 1, wherein at least one of the reactors selected from the dehydrogenation reactor, the first oxidation reactor, or the second oxidation reactor for direct oxidation of saturated hydrocarbon to unsaturated carboxylic acids is a wall reactor, and the dehydrogenation catalyst, the first oxidation catalyst, or the second oxidation catalyst, and the foam body or the foam body coated with the dehydrogenation catalyst, the first oxidation catalyst, the second oxidation catalyst or the catalyst material which catalyses the direct oxidation of a saturated hydrocarbon to an unsaturated carboxylic acid, or that formed from this catalyst material, is localized in the reaction chamber between two adjacent plates.

17. The process according to claim 1, wherein at least two separable foam bodies coated with a catalyst material or formed from this catalyst material are present in at least one of the reactors selected from the dehydrogenation reactor, the first oxidation reactor, the second oxidation reactor or a reactor for direct oxidation of saturated hydrocarbon to unsaturated carboxylic acids.

18. The process according to claim 17, wherein the at least two separable foam bodies coated with the catalyst material or formed from the catalyst material are present as random packings in a fixed bed or as foam body blocks.

19. The process according to claim 17, wherein at least two of the separable foam bodies of one reactor differ by their catalytic activity.

20. The process according to claim 19, wherein the dehydrogenation reactor, the first oxidation reactor, the second oxidation reactor or the reactor for direct oxidation comprise(s) the at least two separable foam bodies coated with the catalyst material or formed from the catalyst material, and wherein the at least two separable foam bodies coated with the catalyst material or formed from the catalyst material are arranged within the dehydrogenation reactor, the first oxidation reactor, the second oxidation reactor or the reactor for direct oxidation such that the catalytic activity per volume element increases in the direction from the reactant inlet to the product outlet.

21. A process for preparing purified unsaturated carboxylic acids, comprising the steps of:
(I) preparing a gas mixture comprising an unsaturated carboxylic acid by a process according to claim 1;
(II) absorbing the unsaturated carboxylic acid in a solvent to obtain a solution comprising an unsaturated carboxylic acid;
(III) removing the unsaturated carboxylic acid from the solution comprising the unsaturated carboxylic acid by means of distillation, extraction, crystallization or a combination of these removal methods.

22. A process for preparing a polymer based on an unsaturated carboxylic acid, comprising the process steps of:
($\alpha$1) preparing a purified unsaturated carboxylic acid by the process according to claim 21;
($\alpha$2) free-radically polymerizing the unsaturated carboxylic acid.

* * * * *